(12) United States Patent
Tran (10) Patent No.: US 8,460,375 B2
(45) Date of Patent: Jun. 11, 2013

(54) LENS DELIVERY SYSTEM

(75) Inventor: Son Trung Tran, Arlington, TX (US)

(73) Assignee: Novartis AG, Lichtstrasse, Basel (CH)

( * ) Notice: Subject to any disclaimer, the term of this patent is extended or adjusted under 35 U.S.C. 154(b) by 1538 days.

(21) Appl. No.: 11/503,851

(22) Filed: Aug. 14, 2006

(65) Prior Publication Data

US 2008/0039862 A1    Feb. 14, 2008

(51) Int. Cl.
*A61F 2/16* (2006.01)

(52) U.S. Cl.
USPC .......................................................... 623/6.12

(58) Field of Classification Search
USPC .................. 606/107, 166; 623/6.12; 206/438, 206/5.1, 263–265; 600/7
See application file for complete search history.

(56) References Cited

U.S. PATENT DOCUMENTS

| | | |
|---|---|---|
| 4,681,102 A | 7/1987 | Bartell |
| 5,026,396 A | 6/1991 | Darin |
| 5,098,439 A | 3/1992 | Hill et al. |
| 5,190,552 A | 3/1993 | Kelman |
| 5,275,604 A | 1/1994 | Rheinish et al. |
| 5,304,182 A | 4/1994 | Rheinish et al. |
| 5,494,484 A | 2/1996 | Feingold |
| 5,499,987 A | 3/1996 | Feingold |
| 5,578,042 A * | 11/1996 | Cumming .................... 606/107 |
| 5,616,148 A | 4/1997 | Eagles et al. |
| 5,620,450 A | 4/1997 | Eagles et al. |
| 5,653,715 A | 8/1997 | Reich et al. |
| 5,716,364 A | 2/1998 | Makker et al. |
| 5,776,138 A | 7/1998 | Vidal et al. |
| 5,820,373 A | 10/1998 | Okano et al. |
| 6,010,510 A | 1/2000 | Brown et al. |
| 6,162,230 A | 12/2000 | Polla et al. |
| 6,228,094 B1 * | 5/2001 | Erdman ........................ 606/107 |
| 6,447,519 B1 * | 9/2002 | Brady et al. .................. 606/107 |
| 6,471,708 B2 | 10/2002 | Green |
| 6,500,181 B1 * | 12/2002 | Portney ........................ 606/107 |
| 6,607,537 B1 | 8/2003 | Binder |
| 6,685,740 B2 | 2/2004 | Figueroa et al. |
| 6,899,717 B2 | 5/2005 | Weber et al. |
| 6,964,648 B2 | 11/2005 | Talling et al. |
| 7,131,976 B2 | 11/2006 | Kobayashi et al. |
| 7,156,854 B2 | 1/2007 | Brown et al. |
| 7,189,218 B2 | 3/2007 | Lichtenberg |
| 7,422,604 B2 | 9/2008 | Vaquero et al. |
| 7,429,263 B2 | 9/2008 | Vaquero et al. |
| 2003/0135221 A1 | 7/2003 | Sabet |
| 2003/0212409 A1 | 11/2003 | Kobayashi et al. |
| 2004/0054374 A1 | 3/2004 | Weber et al. |
| 2004/0087896 A1 | 5/2004 | Wise et al. |

(Continued)

FOREIGN PATENT DOCUMENTS

| EP | 0174917 A | 3/1986 |
|---|---|---|
| EP | 1360944 A2 | 11/2003 |

(Continued)

OTHER PUBLICATIONS

Barakova D., abstract of "Implantation of the AcrySof MA30BA Lens Using the Monarch System," found in PubMed database, May 2002, http://ncbi.nlm.gov/pubmed/12087658 (1 page).

*Primary Examiner* — Thomas McEvoy (57) ABSTRACT

A lens delivery system having a two folding mechanisms. The first mechanism is structured to fold an intraocular lens stabilizing ring, and the second mechanism is designed to fold an intraocular lens.

18 Claims, 7 Drawing Sheets

U.S. PATENT DOCUMENTS

| | | |
|---|---|---|
| 2004/0238392 A1* | 12/2004 | Peterson et al. .............. 206/438 |
| 2005/0049605 A1 | 3/2005 | Vaquero et al. |
| 2005/0049606 A1 | 3/2005 | Vaquero et al. |
| 2005/0143750 A1 | 6/2005 | Vaquero |
| 2005/0149056 A1 | 7/2005 | Rathert |
| 2005/0203619 A1 | 9/2005 | Altmann |
| 2005/0222578 A1* | 10/2005 | Vaquero .................. 606/107 |
| 2005/0222579 A1 | 10/2005 | Vaquero et al. |
| 2006/0063962 A1* | 3/2006 | Drobnik et al. ................ 600/7 |
| 2006/0184181 A1 | 8/2006 | Cole et al. |
| 2006/0200167 A1* | 9/2006 | Peterson et al. .............. 606/107 |
| 2006/0229634 A1 | 10/2006 | Shepherd |
| 2007/0050023 A1 | 3/2007 | Bessiere et al. |
| 2007/0060925 A1 | 3/2007 | Pynson |
| 2007/0173860 A1 | 7/2007 | Iwasaki |
| 2008/0200920 A1 | 8/2008 | Downer |
| 2008/0200921 A1 | 8/2008 | Downer |
| 2008/0221584 A1 | 9/2008 | Downer |
| 2008/0221585 A1 | 9/2008 | Downer |
| 2008/0255577 A1 | 10/2008 | Downer |
| 2009/0043313 A1* | 2/2009 | Ichinohe et al. .............. 606/107 |
| 2009/0112223 A1 | 4/2009 | Downer |
| 2009/0171366 A1* | 7/2009 | Tanaka .................. 606/107 |
| 2009/0204123 A1 | 8/2009 | Downer |

FOREIGN PATENT DOCUMENTS

| | | | |
|---|---|---|---|
| EP | 1360944 | A3 | 11/2003 |
| EP | 1481652 | A1 | 12/2004 |
| EP | 1661533 | A1 | 5/2006 |
| EP | 1891911 | A1 | 2/2008 |
| EP | 1958593 | A1 | 8/2008 |
| EP | 2062552 | A1 | 5/2009 |
| FR | 2820633 | | 8/2002 |
| JP | 2003070829 | A | 3/2003 |
| JP | 2003325569 | A | 11/2003 |
| JP | 2006181269 | | 7/2006 |
| RU | 2138232 | C1 | 9/1999 |
| RU | 2238283 | C2 | 10/2004 |
| RU | 2242956 | C1 | 12/2004 |
| SU | 1440496 | A1 | 11/1988 |
| WO | WO 9407436 | A1 | 4/1994 |
| WO | WO 96/10372 | A1 | 4/1996 |
| WO | WO 98/20819 | A1 | 5/1998 |
| WO | WO 00/40175 | A1 | 7/2000 |
| WO | WO 2005/023154 | A2 | 3/2005 |
| WO | WO 2005/023154 | A3 | 3/2005 |
| WO | WO 2005/102223 | A1 | 11/2005 |
| WO | WO 2006/059183 | A1 | 6/2006 |
| WO | WO 2006/070561 | A1 | 7/2006 |
| WO | WO/2006/080191 | * | 8/2006 |
| WO | WO 2006/113138 | | 10/2006 |
| WO | WO 2006/113357 | A2 | 10/2006 |

* cited by examiner

LENS DELIVERY SYSTEM

This invention relates to intraocular lenses (IOLs) and more particularly to devices use to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in U.S. Pat. No. 4,681,102 (Bartell), and includes a split, longitudinally hinged cartridge. Similar designs are illustrated in U.S. Pat. Nos. 5,494,484 and 5,499,987 (Feingold) and U.S. Pat. Nos. 5,616,148 and 5,620,450 (Eagles, et al.). In an attempt to avoid the claims of U.S. Pat. No. 4,681,102, several solid cartridges have been investigated, see for example U.S. Pat. No. 5,275,604 (Rheinish, et al.) and U.S. Pat. No. 5,653,715 (Reich, et al.).

These devices are designed to implant a single piece or unitary lens. IOL's currently under development include multi-component lenses, such as a lens system having a separate lens and stabilizing ring. Both components must be implanted in the capsular bag and assembled to complete the system. No prior art injection cartridge is capable of injecting all of the components of a multi-component lens system into the capsular bag.

Accordingly, a need continues to exist for a lens delivery system capable of injecting all of the components of a multi-component lens system into the capsular bag.

BRIEF SUMMARY OF THE INVENTION

The present invention improves upon prior art by providing a lens delivery system having a two folding mechanisms. The first mechanism is structured to fold an intraocular lens stabilizing ring, and the second mechanism is designed to fold an intraocular lens.

It is accordingly an object of the present invention to provide a lens delivery system suitable for the storage, shipment and delivery of a lens into an eye without the use of any additional devices.

It is a further object of the present invention to provide a lens delivery system that is suitable for folding lenses made from a soft acrylic material.

It is a further object of the present invention to provide a lens delivery system having a two folding mechanisms.

Other objectives, features and advantages of the present invention will become apparent with reference to the drawings, and the following description of the drawings and claims.

DETAILED DESCRIPTION OF THE INVENTION

Figure 1:
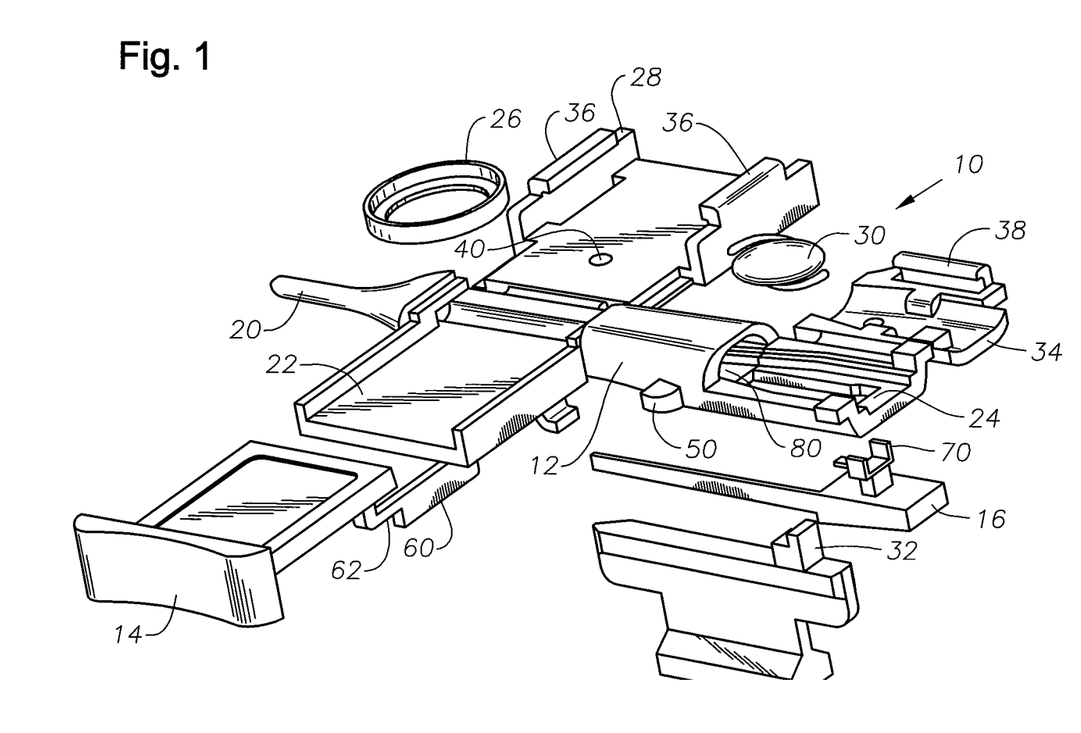
FIG. 1 is an exploded perspective view of the lens delivery system of the present invention shown in an open position.
Figure 3:
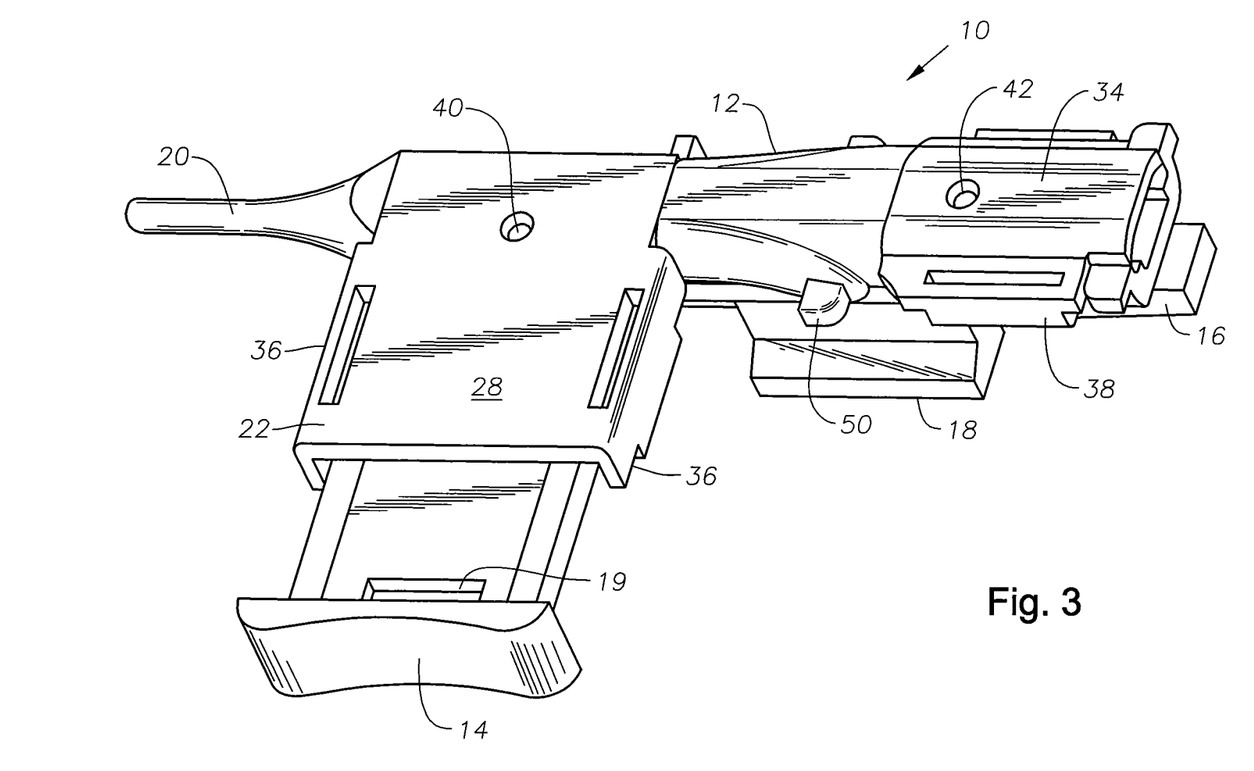
FIG. 3 is a perspective view of the lens delivery system of the present invention shown in a closed position, ready to fold a lens.

As best seen in FIG. 1, lens delivery system 10 of the present invention generally includes cartridge body 12, ring pusher 14, plunger 16 and shipping lock 18. Body 12 generally contains distal nozzle 20, ring folding platform 22 and lens folding platform 24. Ring portion 26 of a multi-component intraocular lens is placed in ring folding platform 22 and secured by ring pusher 14 and by folding ring platform lid 28 over ring folding platform 22 and holding lid 28 in place by clasps 36, thereby encasing ring portion 26 within ring folding platform 22, as seen in FIG. 3. Lens portion 30 of a multi-component intraocular lens is placed in lens folding platform 24 and secured by stop 32 on shipping lock 18 and by folding lens folding platform lid 34 over lens folding platform 24, as seen in FIG. 3. Lid 34 is held in place in the folded position by clasp 38.

Nozzle 20 preferably is hollow on the inside and is of a size suitable for inserting ring portion 26 and lens portion 30 through a relatively small (e.g., on the order of 2 mm or less) incision. Lid 28 and lid 34 may contain ports 40 and 42, respectively, for allowing a viscoelastic material to be introduced into ring folding platform 22 and lens folding platform 24 and around ring portion 26 and lens portion 30.

Figure 5:
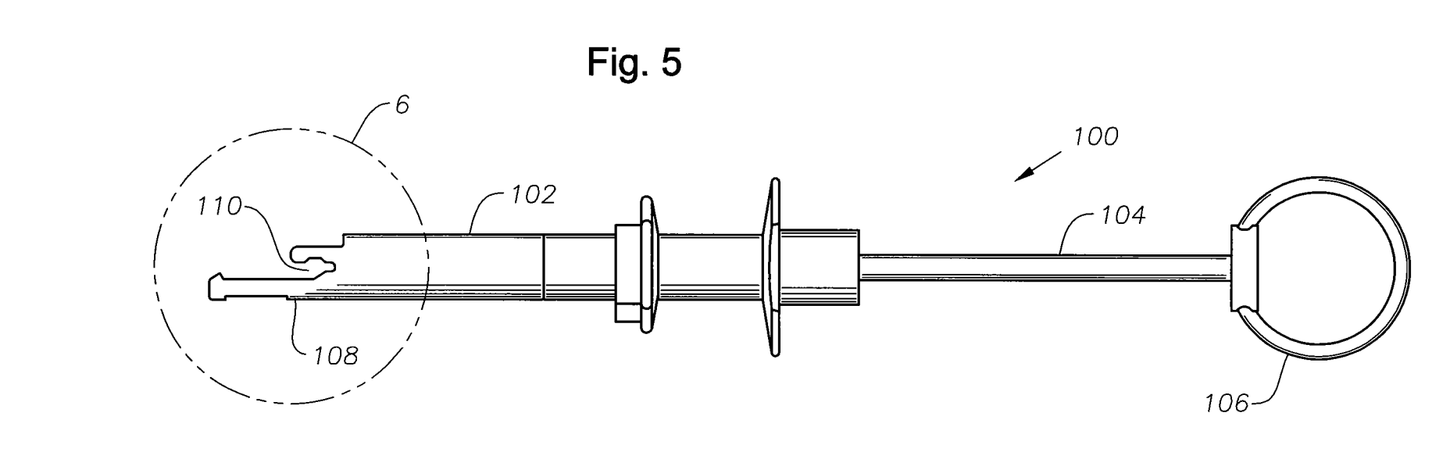
FIG. 5 is a side elevational view of a handpiece that may be used with the lens delivery system of the present invention.
Figure 6:
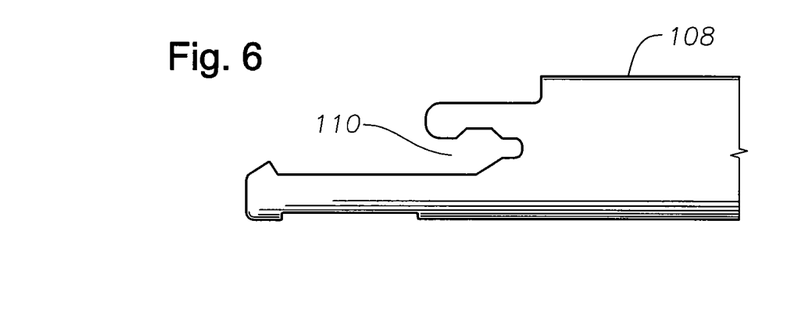
FIG. 6 is an enlarged elevational view of the distal tip of the handpiece taken at circle 6 in FIG. 5.
Figure 7:
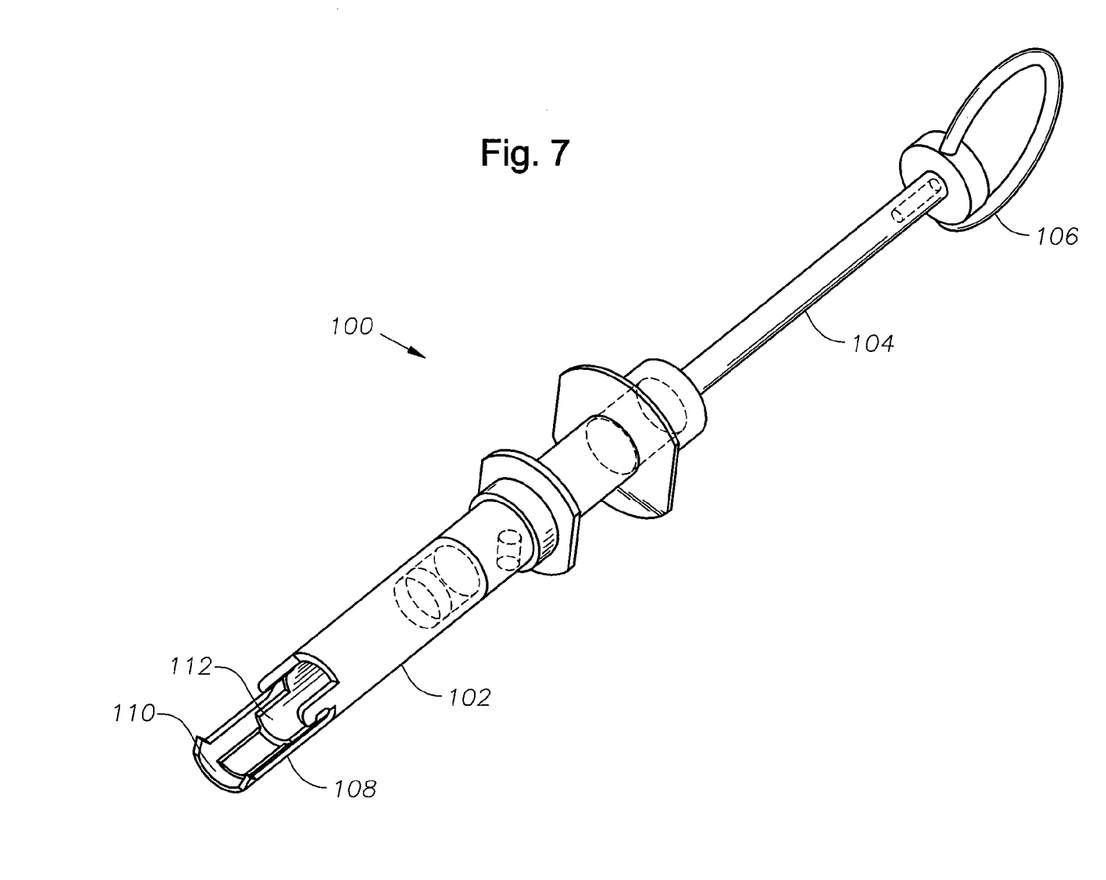
FIG. 7 is a perspective view of a handpiece that may be used with the lens delivery system of the present invention.

As best seen in FIGS. 5 and 6, handpiece 100, which may be used as part of lens delivery system 10 generally consists of tubular body 102, plunger rod 104 and finger ring 106. As been seen in FIG. 6, distal end 108 of body 102 contains notched portion 110 sized and shaped to receive and securely retain body 12, for example, by the use of locking tabs 50 on body 12. Distal end 108 also contains bumper 112, which has the function described below. Plunger rod 104 reciprocates within body 102 by pushing on finder ring 106. Plunger rod 104 may be mounted within body 102 on a spring (not shown) for providing tactile feedback.

Figure 2:
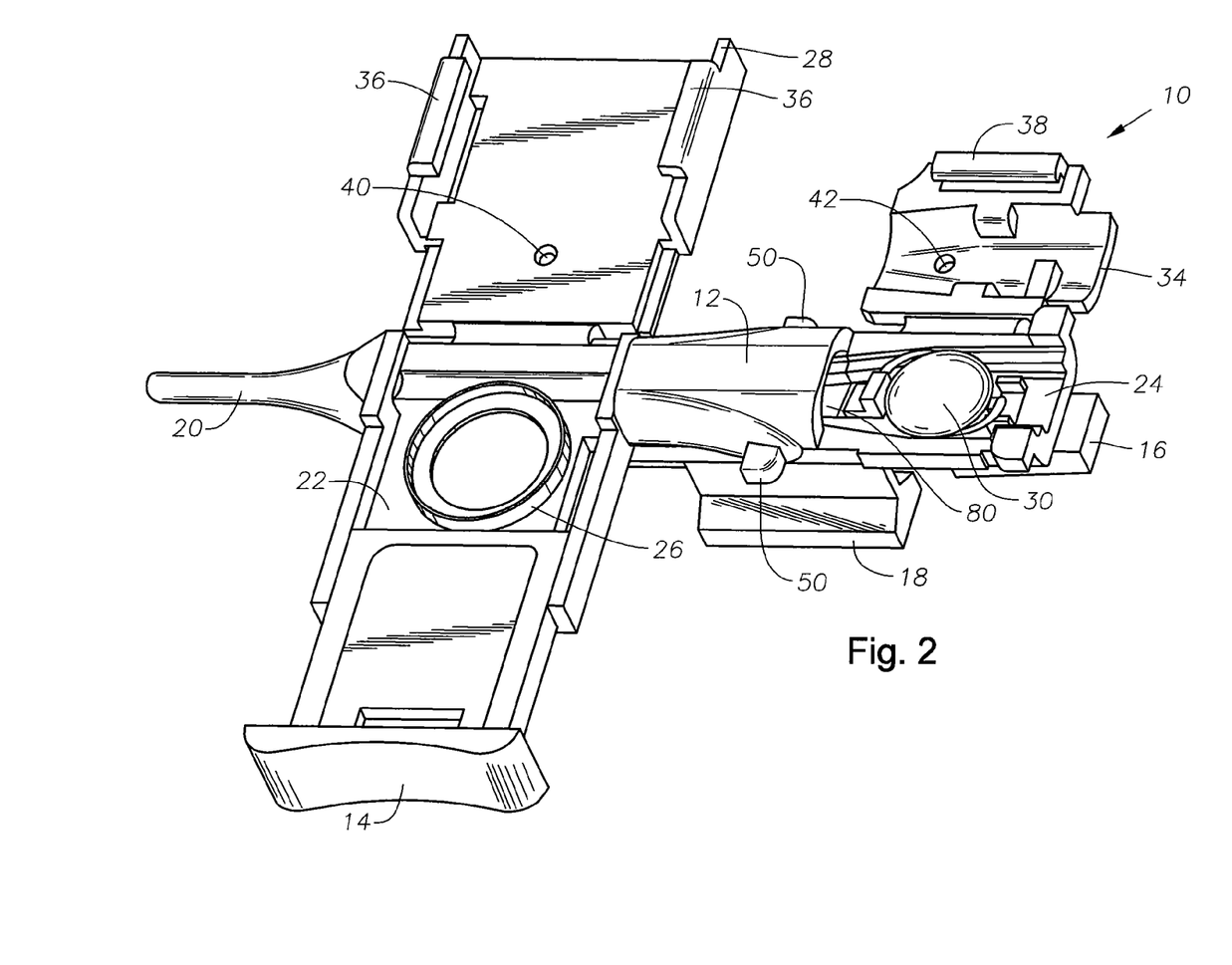
FIG. 2 is a perspective view of the lens delivery system of the present invention shown in an open position.
Figure 4:
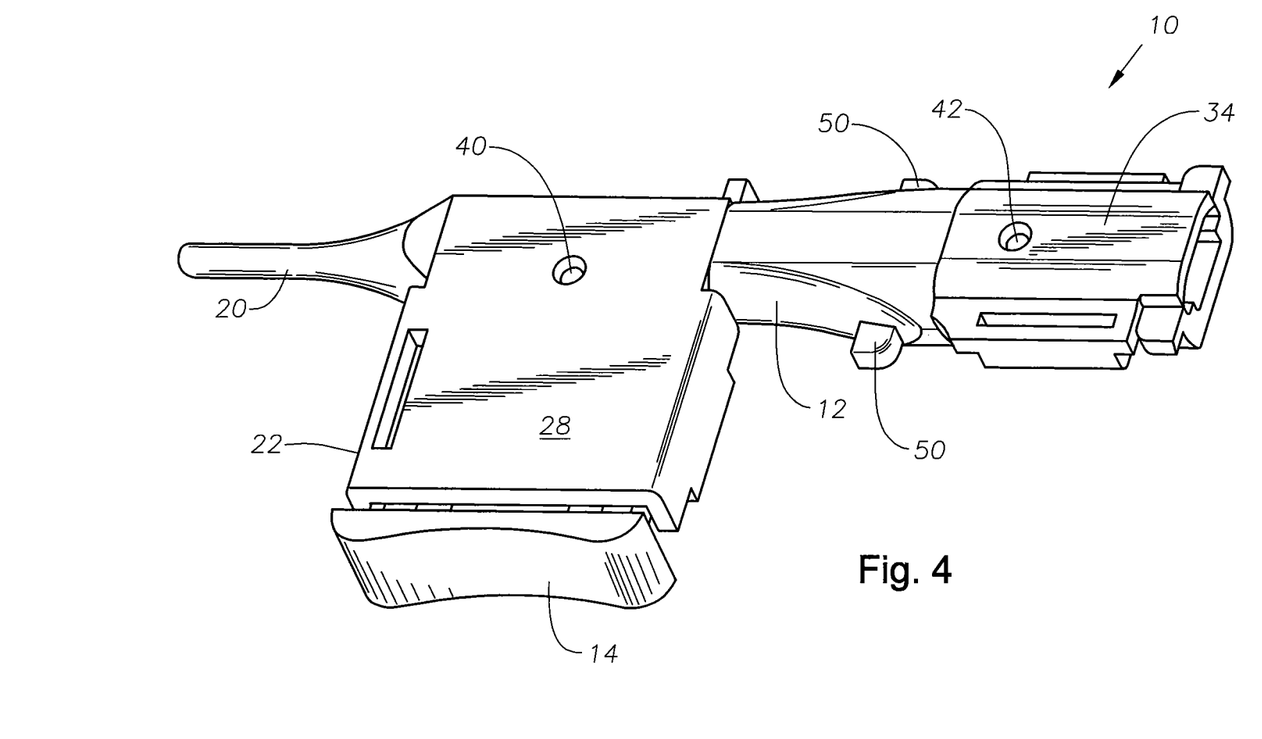
FIG. 4 is a perspective view of the lens delivery system of the present invention shown in a closed position, with the front, or distal folding mechanism having already folding a stabilizing ring portion of an intraocular lens system.
Figure 8:
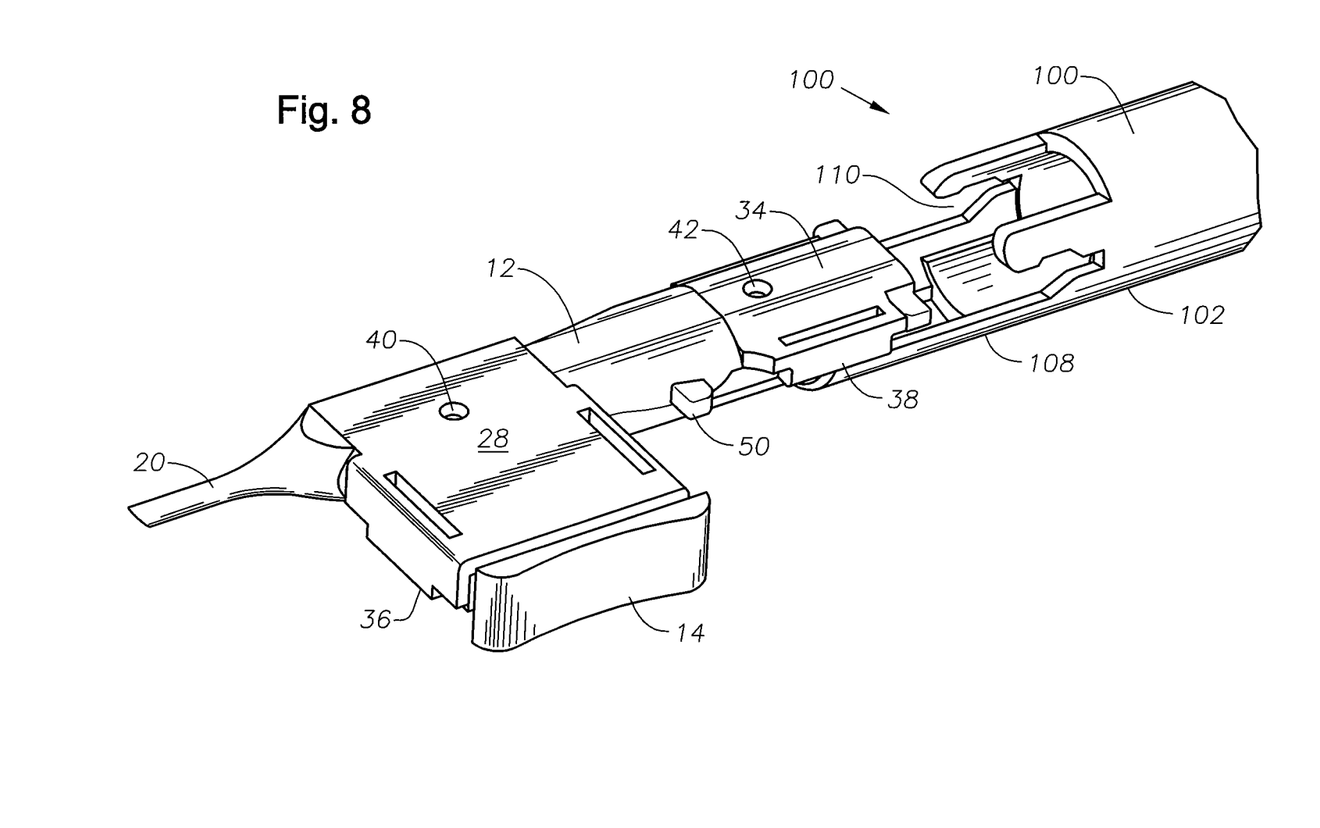
FIG. 8 is an enlarger perspective view of the lens delivery system of the present invention being inserted into the distal end of the handpiece illustrated in FIG. 5.

In use, shipping lock 18 and plunger 16 are installed on body 12 in the manner shown in FIGS. 1 and 2. Ring portion 26 and lens portion 30 are placed in body 12 as shown in FIG. 2 and lids 28 and 34 closed, as shown in FIG. 3. Shipping lock 18 prevents movement of ring pusher 14 during shipment and tab 60 on ring pusher 14 prevents forward movement of plunger 16. Stop 32 and plunger rod guide 70 prevent movement of lens portion 30 during shipment. When ready to be used, shipping lock 18 is removed and ring pusher 14 is pressed inward, as shown in FIG. 4 and locked in place by clasp 19. Such movement of ring pusher 14 collapses or folds ring portion 26, allowing ring portion 26 to fit through nozzle 20. Such movement also aligns notch 62 in tab 60 with plunger 16, allowing plunger 16 to be moved forward. A viscoelastic material is injected through ports 40 and 42 and into nozzle 20. Body 12 is installed within notched portion 110 of distal end 108 of handpiece 100 as shown in FIG. 8. Such installation causes plunger rod 16 to contact and be pushed forward slightly by bumper 112. Such movement pushed lens portion 30 forward slightly, initiating folding of lens portion 30. Plunger rod 104 is advanced and is guided to contact lens portion 30 by rod guide 70. Further movement of plunger rod 104 pushes lens portion 30 through inner bore 80 of body 12 so as to contact compressed ring portion 26 and push ring portion 26, followed by lens portion 30, out of nozzle 20 in a serial manner.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An intraocular lens and intraocular lens delivery system, comprising:
    a multi-component intraocular lens, comprising:
        a ring portion;
        a lens portion; and
    an intraocular lens delivery system, comprising:
        a body, the body having a first platform and a second platform;
        a first lid coupled to the first platform and configured to cover the first platform;
        a second lid coupled to the second platform and configured to cover the second platform, wherein during use the first platform and first lid hold the ring portion detached from the lens portion prior to insertion into an eye and the second lid and second platform hold the lens portion detached from the ring portion prior to insertion into an eye;
        a nozzle on a distal end of the body;
        a ring pusher coupled with the first platform and configured for reciprocal movement within the first platform such that the ring pusher is configured to compress the ring portion between the first lid and first platform; and
        a plunger coupled with the second platform;
        wherein the first platform, the second platform, and the nozzle are coupled together and aligned to allow the ring portion and the lens portion to be pushed out of the nozzle in a serial manner.

2. The lens delivery system of claim 1 wherein the ring pusher contains a tab, the tab preventing movement of the plunger.

3. The lens delivery system of claim 1 wherein the plunger further comprises a rod guide.

4. The lens delivery system of claim 3 further comprising a handpiece having a plunger rod and a notch for receiving the body.

5. The lens delivery system of claim 4 wherein the plunger rod extends through the rod guide when the body is installed in the notch and the plunger rod is advanced through the handpiece.

6. The lens delivery system of claim 1 further comprising a handpiece having a notch for receiving the body.

7. The lens delivery system of claim 6 wherein the handpiece further comprises a bumper that causes movement of the plunger when the body is installed within the notch in the handpiece.

8. The lens delivery system of claim 1, further comprising a removable shipping lock for preventing movement of the ring pusher.

9. The lens delivery system of claim 1, wherein the alignment of the first platform and second platform is configured to allow the ring portion to be pushed out of the nozzle prior to the lens portion.

10. The lens delivery system of claim 1, wherein the first platform, second platform, and nozzle are aligned such that during delivery of the intraocular lens the lens portion passes through the second platform before passing through the first platform and passes through the first platform before passing through the nozzle.

11. An intraocular lens and intraocular lens delivery system, comprising:
    a multi-component intraocular lens, comprising:
        a ring portion;
        a lens portion; and
    an intraocular lens delivery system, comprising:
        a body, the body having a first platform and a second platform;
        a first lid coupled to the first platform and configured to cover the first platform;
        a second lid coupled to the second platform and configured to cover the second platform, wherein during use the first platform and first lid hold the ring portion separate from the lens portion prior to insertion into an eye and the second lid and second platform hold the lens portion separate from the ring portion prior to insertion into an eye;
        a nozzle on a distal end of the body;
        a ring pusher having a tab, the ring pusher coupled with the first platform and configured for reciprocal movement within the first platform such that the ring pusher is configured to compress the ring portion between the first lid and first platform prior to insertion;
        a plunger having a rod guide coupled with the second platform; and
        a removable shipping lock for preventing movement of the ring pusher prior to insertion;
        wherein the first platform, the second platform, and the nozzle are coupled together and aligned to allow the ring portion and the lens portion to be pushed out of the nozzle in a serial manner.

12. The lens delivery system of claim 11 further comprising a handpiece having a notch for receiving the body.

13. The lens delivery system of claim 12 wherein the handpiece further comprises a bumper that causes movement of the plunger when the body is installed within the notch in the handpiece.

14. The lens delivery system of claim 11 further comprising a handpiece having a plunger rod and a notch for receiving the body.

15. The lens delivery system of claim 14 wherein plunger rod extends through the rod guide when the body is installed in the notch and the plunger rod is advanced through the handpiece.

16. The lens delivery system of claim 11 wherein the shipping lock has a stop to help prevent movement of the lens portion of the intraocular lens contained within the second platform.

17. The lens delivery system of claim 11, wherein the alignment of the first platform and second platform is configured to allow the ring portion to be pushed out of the nozzle prior to the lens portion.

18. The lens delivery system of claim 11, wherein the first platform, second platform, and nozzle are aligned such that during delivery of the intraocular lens the lens portion passes through the second platform before passing through the first platform and passes through the first platform before passing through the nozzle.

* * * * *

UNITED STATES PATENT AND TRADEMARK OFFICE
CERTIFICATE OF CORRECTION

| | | |
|---|---|---|
| PATENT NO. | : 8,460,375 B2 | Page 1 of 1 |
| APPLICATION NO. | : 11/503851 | |
| DATED | : June 11, 2013 | |
| INVENTOR(S) | : Tran | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1566 days.

Signed and Sealed this
Thirtieth Day of December, 2014

Michelle K. Lee
*Deputy Director of the United States Patent and Trademark Office*